(12) United States Patent
Bars

(10) Patent No.: US 9,987,414 B2
(45) Date of Patent: Jun. 5, 2018

(54) SYSTEM FOR DELIVERY OF FLUIDS SUCH AS AMMONIA NITROGEN 13

(71) Applicant: Erol Bars, Grand Island, NY (US)

(72) Inventor: Erol Bars, Grand Island, NY (US)

(*) Notice: Subject to any disclaimer, the term of this patent is extended or adjusted under 35 U.S.C. 154(b) by 386 days.

(21) Appl. No.: 14/820,260

(22) Filed: Aug. 6, 2015

(65) Prior Publication Data
US 2016/0038669 A1    Feb. 11, 2016

Related U.S. Application Data

(60) Provisional application No. 62/034,632, filed on Aug. 7, 2014.

(51) Int. Cl.
| | |
|---|---|
| G01N 1/10 | (2006.01) |
| A61M 5/00 | (2006.01) |
| A61M 5/315 | (2006.01) |
| A61M 5/24 | (2006.01) |
| A61M 5/145 | (2006.01) |

(52) U.S. Cl.
CPC ............ A61M 5/007 (2013.01); A61M 5/008 (2013.01); A61M 5/31578 (2013.01); *A61M 2005/14573* (2013.01); *A61M 2005/2474* (2013.01)

(58) Field of Classification Search
CPC ...................................................... G01N 1/10
USPC ....................................................... 436/180
See application file for complete search history.

(56) References Cited

U.S. PATENT DOCUMENTS

| | | | | |
|---|---|---|---|---|
| 4,296,785 A * | 10/1981 | Vitello | ..................... | G21G 4/08 137/625.47 |
| 4,833,329 A * | 5/1989 | Quint | ..................... | G21G 4/08 137/573 |
| 4,853,546 A * | 8/1989 | Abe | ..................... | G01N 1/38 250/432 PD |
| 5,039,863 A * | 8/1991 | Matsuno | ..................... | G01N 1/38 250/432 PD |
| 5,358,691 A | 10/1994 | Clark et al. | | |
| 5,468,355 A * | 11/1995 | Shefer | ..................... | G21G 1/10 204/157.2 |
| 5,598,449 A * | 1/1997 | Yamazaki | ..................... | G21G 1/10 376/195 |
| 5,601,707 A | 2/1997 | Clay et al. | | |
| 5,911,252 A * | 6/1999 | Cassel | ..................... | B65B 3/003 141/234 |
| 6,915,823 B2 * | 7/2005 | Osborne | ..................... | B01F 13/1072 141/104 |
| 7,235,216 B2 * | 6/2007 | Kiselev | ..................... | A61J 3/00 422/159 |
| 7,586,102 B2 * | 9/2009 | Mourtada | ..................... | G21G 1/0005 250/251 |
| 7,718,436 B2 * | 5/2010 | Zigler | ..................... | G01N 35/1079 376/194 |
| 7,734,331 B2 * | 6/2010 | Dhawale | ..................... | G01T 1/00 600/431 |
| 8,286,671 B1 * | 10/2012 | Strangis | ..................... | B65B 7/28 141/104 |

(Continued)

*Primary Examiner* — Arlen Soderquist
(74) *Attorney, Agent, or Firm* — Del Vecchio and Stadler LLP

(57) ABSTRACT

This invention is directed to a delivery system that is able to deliver fluids, namely, ammonia nitrogen 13. Moreover, the delivery system is self-contained, manually portable, and capable of safely and effectively delivering ammonia nitrogen 13. Finally, the delivery system is capable of supplying up to 20 vials of fluid.

11 Claims, 11 Drawing Sheets

(56) References Cited

U.S. PATENT DOCUMENTS

| | | | |
|---|---|---|---|
| 8,435,454 B2* | 5/2013 | Elizarov | B01J 19/0093 422/130 |
| 8,517,905 B2* | 8/2013 | Buck | A61M 5/1407 600/1 |
| 8,821,718 B2* | 9/2014 | Blomberg | G01N 30/88 137/343 |
| 9,139,316 B2* | 9/2015 | Husnu | B65B 3/003 |
| 9,627,097 B2* | 4/2017 | Jackson | G01T 1/00 |
| 2002/0106046 A1* | 8/2002 | Fujimoto | G21G 1/02 376/156 |
| 2004/0022696 A1* | 2/2004 | Zigler | G01N 35/1079 422/159 |
| 2004/0258615 A1* | 12/2004 | Buchanan | A61K 51/0402 424/1.11 |
| 2005/0232387 A1* | 10/2005 | Padgett | A61K 51/0491 376/194 |
| 2005/0277833 A1* | 12/2005 | Williams, Jr. | A61M 5/16827 600/431 |
| 2006/0039522 A1 | 2/2006 | Bars et al. | |
| 2008/0035542 A1* | 2/2008 | Mourtada | G21G 1/0005 210/143 |
| 2008/0177126 A1* | 7/2008 | Tate | A61M 5/172 600/5 |
| 2008/0233018 A1* | 9/2008 | van Dam | B01J 19/0093 422/159 |
| 2008/0242915 A1* | 10/2008 | Jackson | G01T 1/00 600/4 |
| 2009/0094940 A1* | 4/2009 | Py | A23L 2/46 53/267 |
| 2009/0131862 A1* | 5/2009 | Buck | A61M 5/1407 604/67 |
| 2010/0121184 A1* | 5/2010 | Dhawale | G01T 1/00 600/431 |
| 2011/0150714 A1* | 6/2011 | Elizarov | B01J 19/0093 422/159 |
| 2012/0222774 A1* | 9/2012 | Husnu | B65B 3/003 141/69 |
| 2012/0241042 A1* | 9/2012 | Strangis | B65B 7/28 141/2 |
| 2013/0225903 A1* | 8/2013 | Franci | B65B 3/003 600/4 |
| 2013/0337493 A1* | 12/2013 | Hansteen | G01N 21/31 435/34 |
| 2015/0086476 A1* | 3/2015 | Eriksson | C07B 59/00 424/1.11 |

* cited by examiner

SYSTEM FOR DELIVERY OF FLUIDS SUCH AS AMMONIA NITROGEN 13

CROSS-REFERENCE TO RELATED APPLICATIONS

This application claims the benefit of U.S. Provisional Application No. 62/034,632, filed on Aug. 7, 2014, the entire disclosure and contents of which are incorporated by reference.

FIELD OF INVENTION

This invention is directed to a delivery system that is able to safely and effectively deliver fluids, such as, ammonia nitrogen 13.

BACKGROUND OF INVENTION

Positron Emission tomography (PET) imaging is an imaging technique that produces a three-dimensional image of body functioning. When a positron-emitting radioactive isotope (a tracer) is injected into the body on a biologically active molecule, a pair of gamma rays is indirectly emitted by the tracer. The pair of gamma rays is detected by the PET system and thusly provides an image of the body functioning.

A positron is a subatomic particle with the same mass as an electron and has an electronic charge of +1e, so the charge is numerically equal to an electron, but the positron has a positive charge. A positron is also called an anti-electron.

Positron emission is a type of radioactive decay. This occurs when a proton inside a radioactive isotope nucleus is converted to a neutron while releasing a positron and an electron neutrino. Gamma rays are also emitted during this decay. Gamma rays emit electromagnetic radiation at a high frequency.

Ammonia nitrogen 13 can be used for diagnostic purposes in positron emission tomography (PET) imaging. It is used in diagnosing cardiac disease and other cardiac-related problems in patients. In particular, ammonia nitrogen 13 is suitable for myocardial perfusion imaging by (PET).

When injected, ammonia nitrogen 13 is a positron emitting radiopharmaceutical. Nitrogen 13 decays by emitting a positron to Carbon 13. Nitrogen 13 is the longest-lived of the nitrogen radioisotopes, having a half-life of a bit less than ten minutes (9.965 minutes). While nitrogen 13 has the longest half-life of the nitrogen radioisotopes, the half-life of nitrogen 13 is rather short.

As a result of the very short half-life, the ammonia nitrogen 13 needs to be made as close to a PET suite as possible. Ammonia nitrogen 13 is produced in a cyclotron by bombarding water with protons producing a nuclear reaction. The result is ammonia nitrogen 13 and nitride and nitrite impurities.

Thus, if a PET suite uses ammonia nitrogen 13, then there needs to be a cyclotron within 15 minutes of the PET suite. Moreover, there needs to be system capable of purifying the ammonia nitrogen 13 before it is used in the PET application.

Overall, the process of producing ammonia nitrogen 13 for use in PET applications typically includes the use of a cyclotron to bombard oxygen 16 with hydrogen protons thereby producing nitrate and ammonia. Nitrogen 13 is a cyclotron produced radionuclide by a 16 O (p, α) 13 N irradiation reaction with protons. That is, when oxygen 16 is bombarded with protons, it causes the emission of α-particles and production of nitrogen 13. In PET applications nitrogen 13 is used as ammonia nitrogen 13. The reaction to produce nitrogen 13 is:

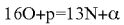

Once the nitrogen 13 is produced, ammonia nitrogen 13 is produced by reduction of nitrogen 13 labeled nitrates and nitrites. Nitrogen 13 is converted to ammonia nitrogen 13 in aqueous medium, which is an exothermic reaction. In this reaction the major chemical species produced are nitrates, nitrites, ammonia and hydroxyl amine. Among them, the nitrates have the highest yield. The hydrogen evolved flushes out the ammonia nitrogen 13 and dissolves in saline solution. The mixture is passed through an anion-exchange resin to remove all anionic impurities, including nitrates and nitrites. The ammonia nitrogen 13 is filtered before use. Then, ammonia nitrogen 13 from the [13N] NH4+target appears in the desired chemical form. It needs to be trapped and filtered by passage through appropriate columns before being mixed with the correct substrate for dispensing NH3 in the form of NH4+ions.

More recently, the development of small cyclotrons has made it more desirable for hospitals or medical facilities to have on-site ammonia nitrogen 13 production for distribution to local PET suites. This has given rise to the need for the PET suite to have a suitable apparatus for purifying the ammonia nitrogen 13 and supplying it into a vial for use by the PET operator.

Previously, most such apparatuses were able to process only two vials of ammonia nitrogen 13 at a time. More recently, the apparatuses were able to process six vials of ammonia nitrogen 13 at a time.

That is, up to this point, most systems that are suited to delivering dosages of ammonia nitrogen 13 for purposes of PET imaging for cardiac patients are only capable of providing up to six dosages at a time. Moreover, these systems are not able to ensure minimal exposure to the radiation from ammonia nitrogen 13.

Thus, there is a need for a system that is capable of providing on demand ammonia nitrogen 13, while decreasing exposure to radiation.

SUMMARY OF THE INVENTION

Accordingly, it is the subject of this invention to provide a system capable of providing on demand ammonia nitrogen 13, while decreasing or eliminating exposure to radiation. Another subject of this invention is to provide a manually portable system for ammonia delivery.

DETAILED DESCRIPTION OF THE INVENTION

Figure 1:
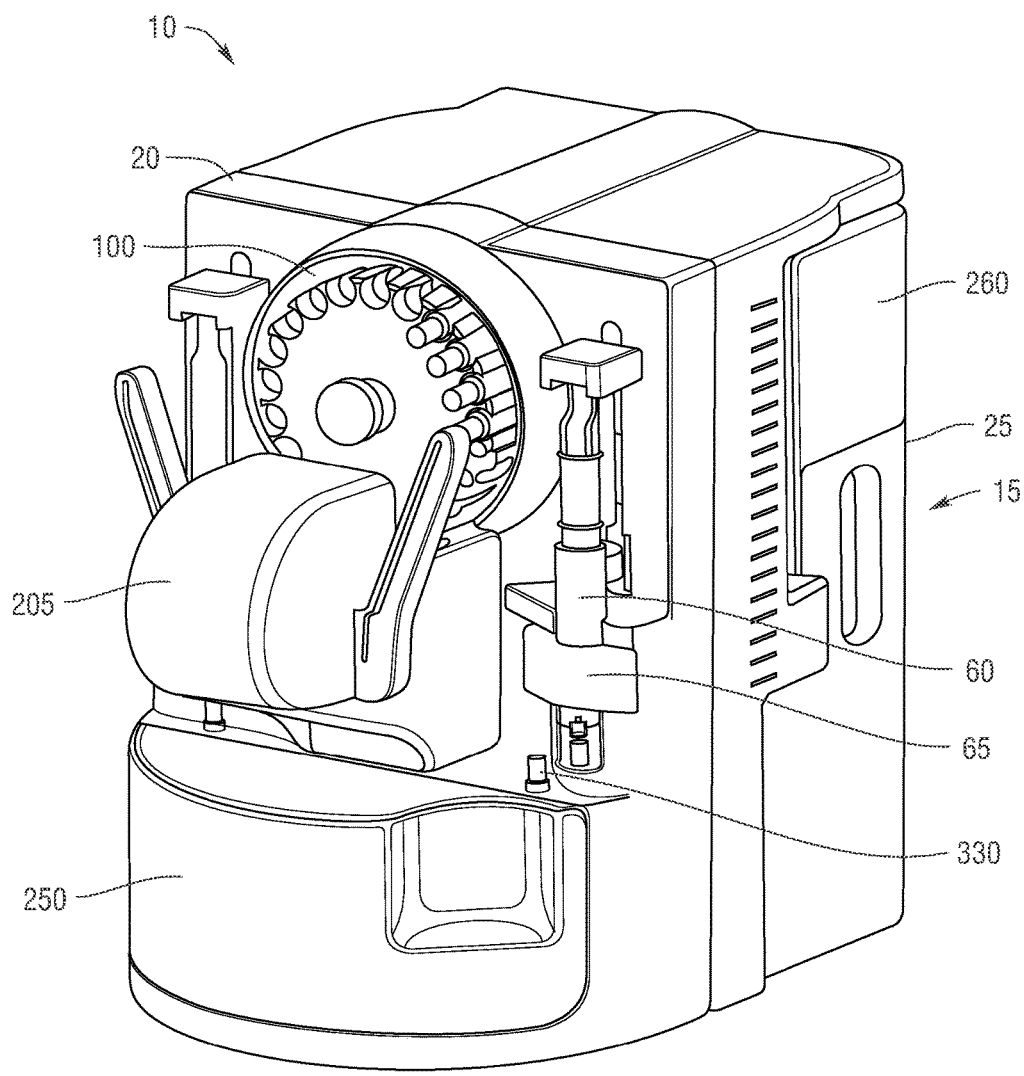
FIG. 1 depicts a system for delivering ammonia nitrogen 13.

The term "ammonia nitrogen 13" as used in this application means ammonia ($NH_3$) wherein the nitrogen has a mass number of 13. The mass number is the total number of protons and neutrons in the atomic nucleus. Nitrogen 13 has 7 protons and 6 neutrons and thus a mass number of 13. Numeral 13 that appears throughout this application is not a reference number.

The term "Servo" as used in this application means servomechanism or servomotor.

A delivery system 10 for delivering ammonia nitrogen 13 is disclosed. The delivery system 10 is a self-contained system that is manually portable. The delivery system 10 has additional benefits including being able to load 20 vials with ammonia nitrogen 13 without having to reload the system. This minimizes, if not eliminates, exposure to radiation. The delivery system 10 also has a single point waste location. Finally, the delivery system 10 provides on-site and on demand ammonia nitrogen 13.

It is noted that the delivery system 10 of the present disclosure is capable of supplying other fluids as well including sodium fluoride.

The delivery system 10 operates by utilizing a series of input and output lines. The delivery system 10 is divided into two major components, a front box 15 and a central support member 20. It is approximately 18 inches tall, 12 inches wide and has a depth of 19 inches. Thus, the delivery system 10 is capable of being manually transported. Of course, the size of the delivery system can be changed and is not so limited to the dimensions just listed.

Turning to FIG. 1, a front view of a delivery system 10 is depicted. Also depicted are several major components of the delivery system 10, including a front box 15 having a front box housing 25, a central support member 20, a reel assembly 100, a gun assembly housing 205, and a valve cover 250.

Figure 2:
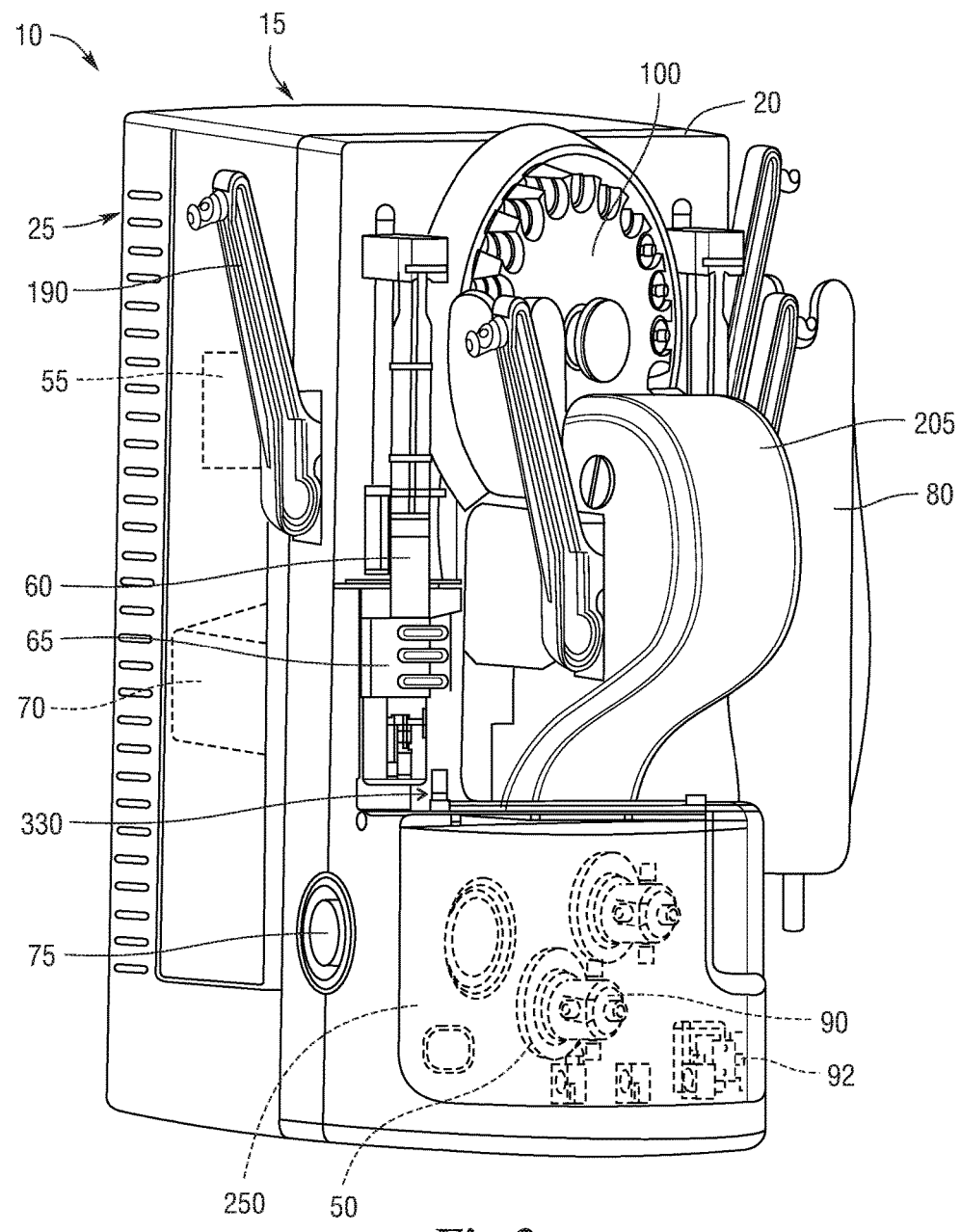
FIG. 2 depicts a rear view of the system for delivering ammonia nitrogen 13.

Turning to FIG. 2, a rear perspective view of the delivery system 10 is illustrated and includes the front box 15, the central support member 20, the front box housing 25, a hook bag 190, syringes 60, clip holders 65, Peek fittings 330, a power supply 70, a helium regulator 75, a gun servo 50, a 4 way rotary valve 90, a 2 way solenoid valve 92, a sterile water bag 80, and the gun assembly housing 205. The delivery system also contains a saline water bag (not shown). PEEK fittings are well known to those having ordinary skill in the art and are commercially available.

Figure 3:
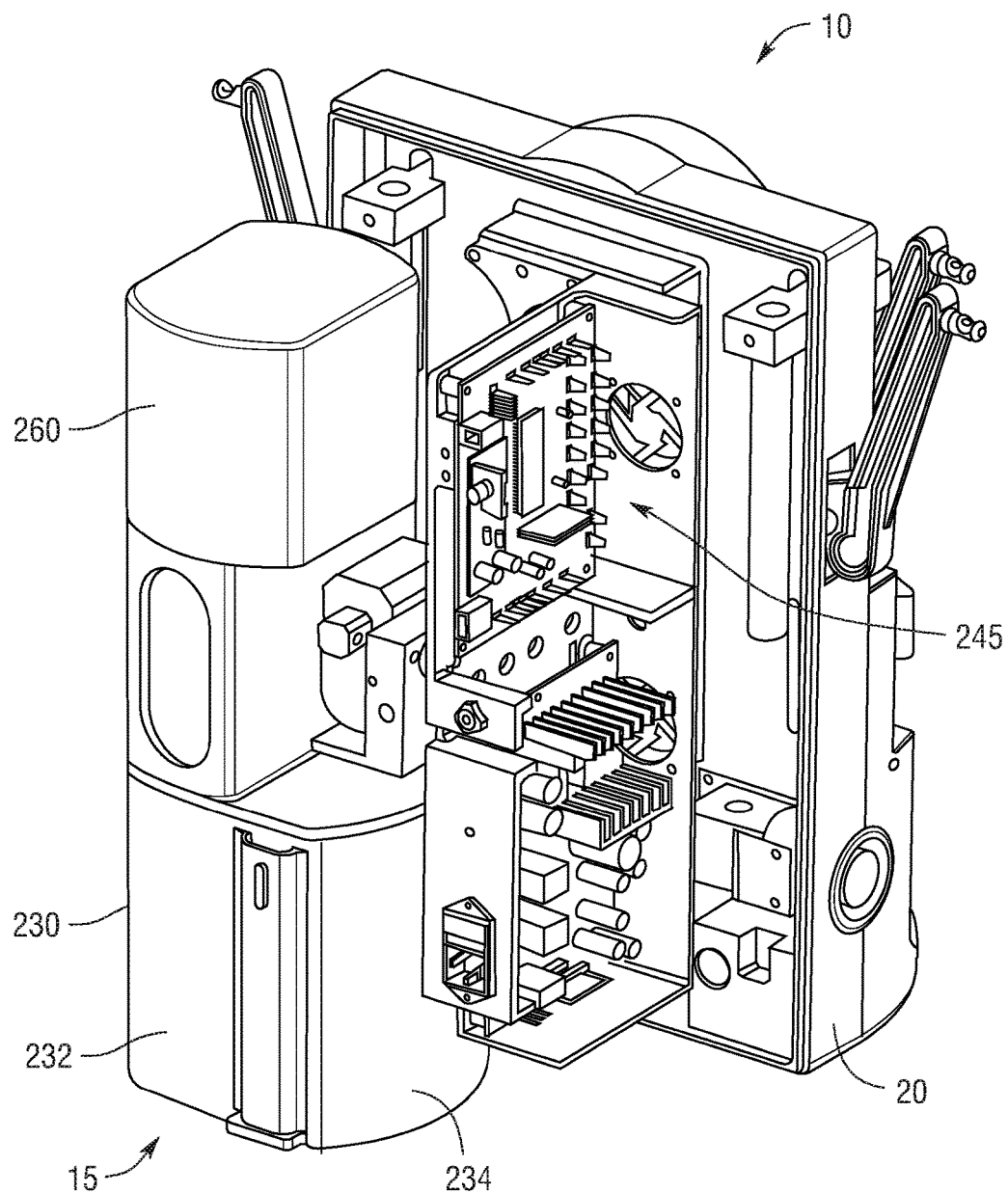
FIG. 3 depicts a front box of the system for delivering ammonia nitrogen.

FIG. 3 depicts a front perspective view of the delivery system 10. The front box 15 contains a waste carafe 230, a waste carafe interior 232, a waste cartridge passageway 234, a water rinse compartment 260, and a computerized control system 245.

Figure 4:
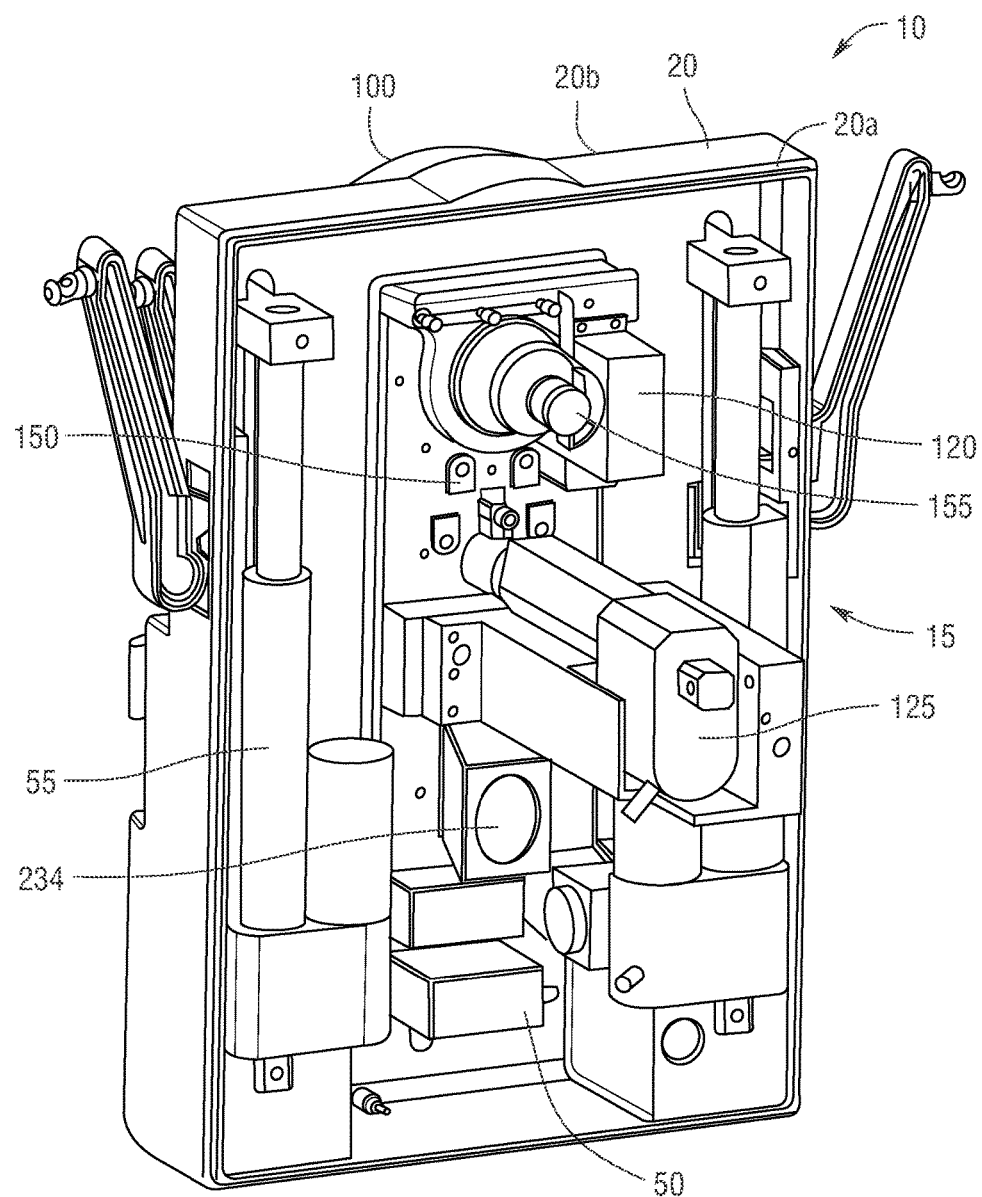
FIG. 4 depicts a back box of the system for delivering ammonia nitrogen 13.

FIG. 4 depicts the interior of the delivery system 10. The central support member 20 supports the following major components: a reel assembly 100, a servo drive 120, which drives a cartridge reel 105 (see FIG. 8), a potentiometer 155, which provides feedback regarding the angular sensor position of the reel assembly 100 (see FIG. 8), a linear electric actuator 125, which provides for a fluid line 130 (see FIG. 8) connection to the back of a cartridge 110 (see FIG. 8), a servo drive 50, a linear electric actuator 55, which supplies the syringes 60, and optic sensors 150, which provide for cartridge 110 detection.

In a preferred embodiment, the cartridges 110 are anion cartridges. In another preferred embodiment, the cartridge reel 105 has 20 cartridge receiving recesses 108 (see FIG. 7) to hold the cartridges 110. The delivery system 10 locates different types of cartridges 110 by optic sensor 150. Optic sensor 110 provides information about the presence or absence of the cartridge 110.

Figure 5:
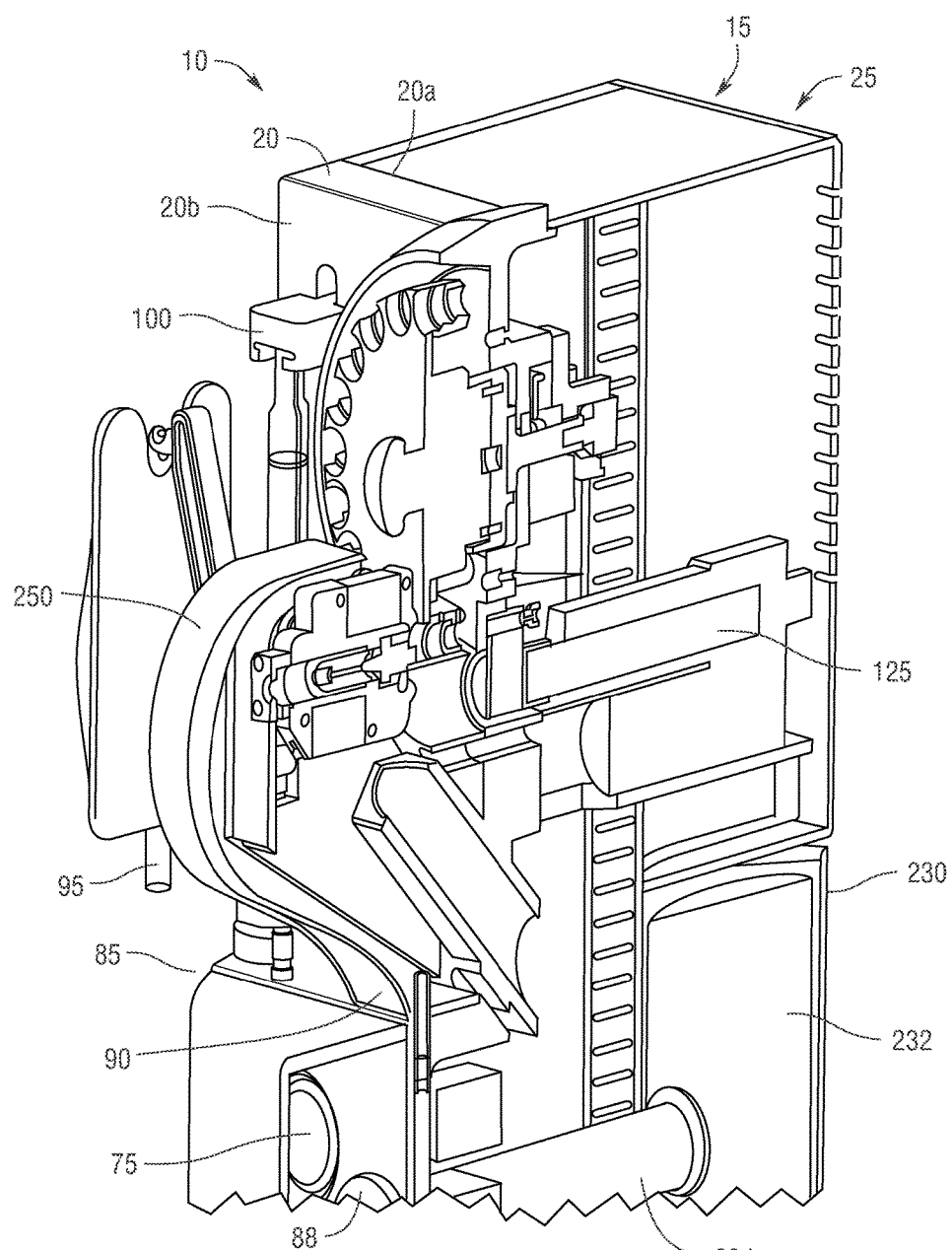
FIG. 5 depicts a rear view of the major components of the delivery system for ammonia nitrogen 13.

FIG. 5 is a cross section of a delivery system 10 with a front box 15 and front box housing 25 and central support member 20. The central support member 20 has opposed first and second sides 20a, 20b. A cross section of the reel assembly 100 is shown along with a cross section of the linear actuator 125. A gun assembly housing 250 is shown having a helium input line 85 connected to a helium regulator 75 and an ammonia nitrogen 13 output line 90, which supplies vial 95 with the ammonia nitrogen 13 (also referred to as input product). A feed through channel 88 contains other input lines (not shown) and output lines (not shown).

In another embodiment, the delivery system 10 includes additional components such as a saline bag (not shown) with a sensor (not shown), a syringe pump (not shown) with a sensor (not shown) for the saline bag, a syringe pump (not shown) with a sensor (not shown) for the sterile water bag 80, a gas helium tank (not shown) with a pressure gauge (not shown) and helium regulator 75 and in fluid communication with a valve (not shown), an input line (not shown) for ammonia nitrogen 13 to enter the delivery system 10, an input line (not shown) for saline to enter the delivery system 10, an input line (not shown) for sterile water to enter the delivery system 10, and input line (not shown) with a sensor (not shown) for helium to enter the delivery system 10, a first sterile vial (not shown) with a sensor (not shown) for receiving ammonia nitrogen 13, saline, sterile water, and helium, a line (not shown) with a sensor (not shown) from the sterile vial (not shown) to a plug (not shown), which holds ammonia nitrogen 13, a line (not shown) with a sensor (not shown) from the plug to a second sterile vial (not shown) for holding the ammonia nitrogen 13, a line (not shown) from the plug to a waste carafe 230 with a sensor (not shown) to hold the water and saline waste, a line (not shown) from the second sterile vial to a third sterile vial (not shown) with a sensor (now shown). In a preferred embodiment, the saline bag is 250 ml in size and the sterile water bag is 500 ml in size.

Figure 6:
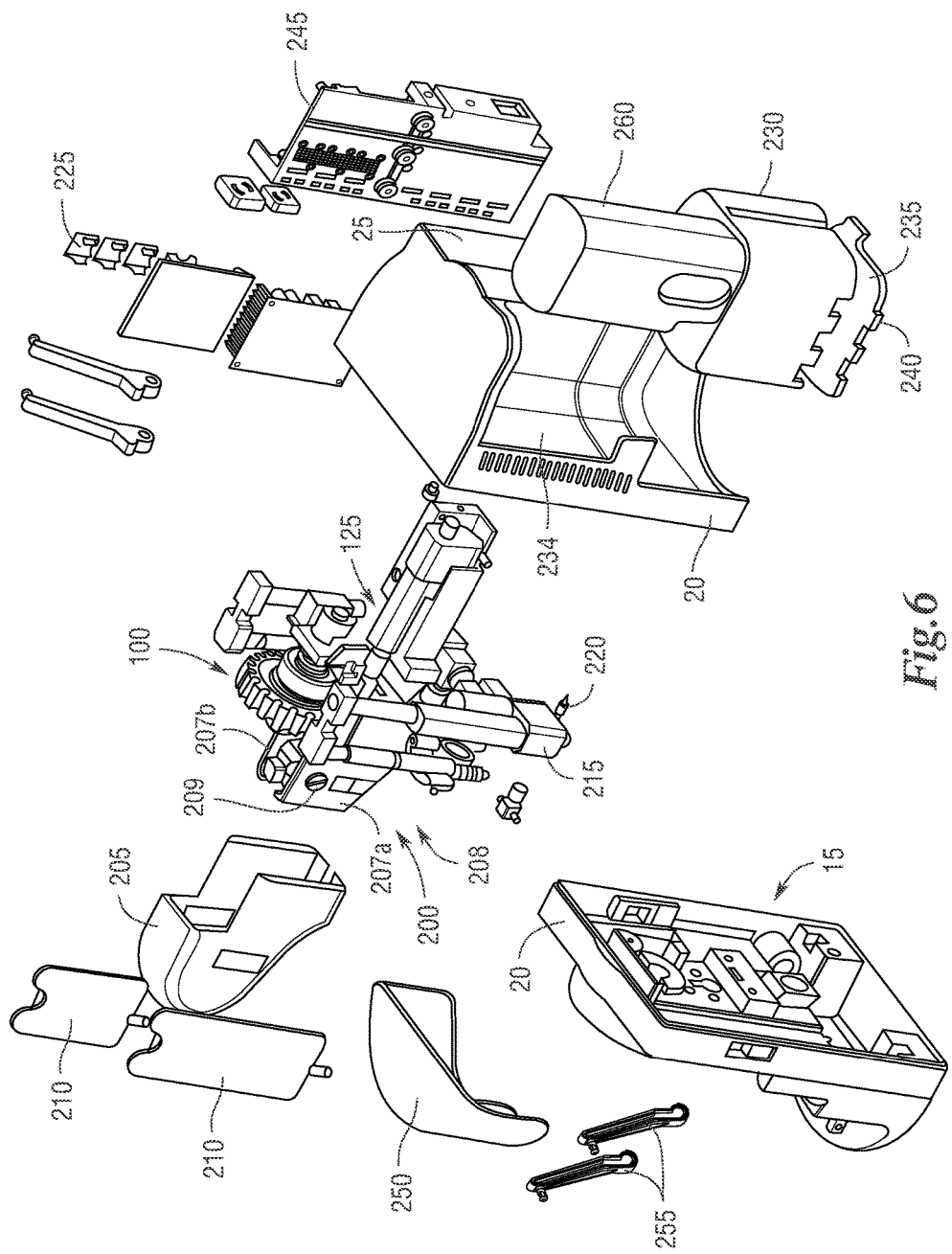
FIG. 6 depicts an exploded view of the components of the delivery system for ammonia nitrogen 13.

Turning to FIG. 6, an exploded view of the delivery system 10 is depicted, wherein the major components of the delivery system 10 are also shown, including a front box 15 of the delivery system 10. A gun assembly 200 is covered by a gun assembly housing 205, which is held in place by magnets 210. A gun 200, which is supported by spaced apart gun mounts 207a and 207b connected by a pivot rod 209 and has a gun housing interior 208 defined therein. A linear actuator 215 for rotating the gun assembly 200 is also depicted and is in communication with a switch 220 for carafe detection. Also shown is a PCB driver 225 for the linear actuator 125 for the reel assembly 100. A waste carafe 230 is shown having a bottom waste door trap 235, which is held by magnets 240. Finally, a valve cover 250 is shown, which is held in place by magnets 255.

Figure 7:
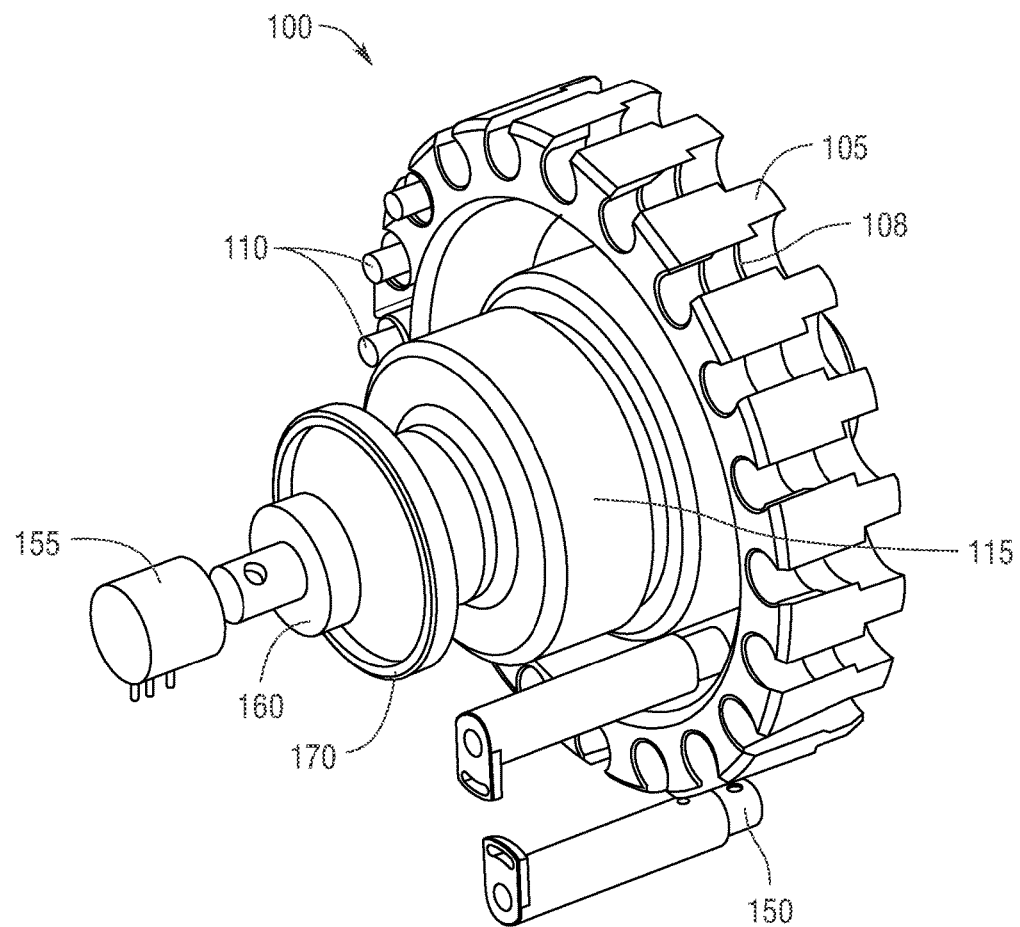
FIG. 7 is a rear perspective view of a cartridge reel.

FIG. 7 depicts an exploded view of the reel assembly 100. The major components of reel assembly 100 include a cartridge reel 105 having cartridge receiving recesses 108, a reel junction base 115, optic sensors 150, cartridges 110, a potentiometer 155, a shaft bearing 160, and a gear drive 170.

As explained above, the potentiometer 155 senses the angular position of the sensors 150. The shaft bearing 160 and the gear drive 170 move the cartridge reel 105 so that the cartridges 110 may be inserted into the cartridge reel 105 or pushed out of the cartridge reel 105.

Figure 8:
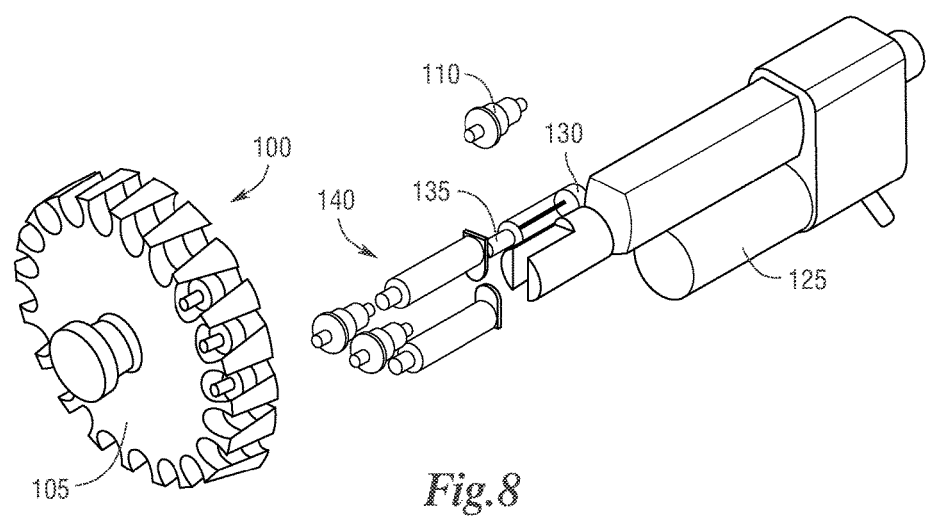
FIG. 8 depicts a reel assembly of the system for delivering ammonia nitrogen 13.

In FIG. 8, an exploded view of the cartridge reel 105 of the cartridge reel assembly 100 is depicted. A cartridge reel linear actuator 125 is connected to input product line 130, which fills cartridge 110, which is then pushed into the reel selector 105 by pin pusher 135, which pushes pin 140.

Figure 9:
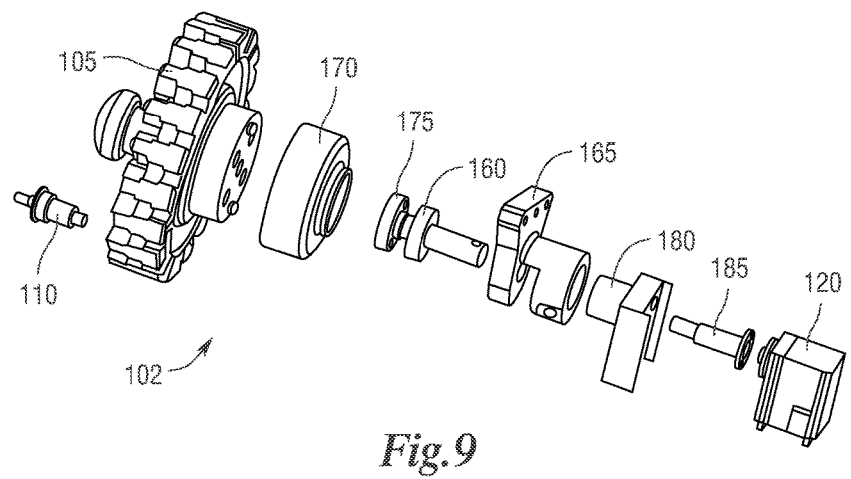
FIG. 9 depicts an exploded view of the reel assembly.

In FIG. 9, a cartridge reel driver assembly 102 is depicted, which includes the cartridge reel 105, the cartridges 110, a coupling 170, which ultimately couples the cartridge reel 105 to the servo 120. Within the cartridge reel driver assembly there is also a coupling shaft 175, a bearing shaft 160, a bearing shaft bracket 165, a servo casing 180, and a servo shaft coupling 185.

Figure 10:
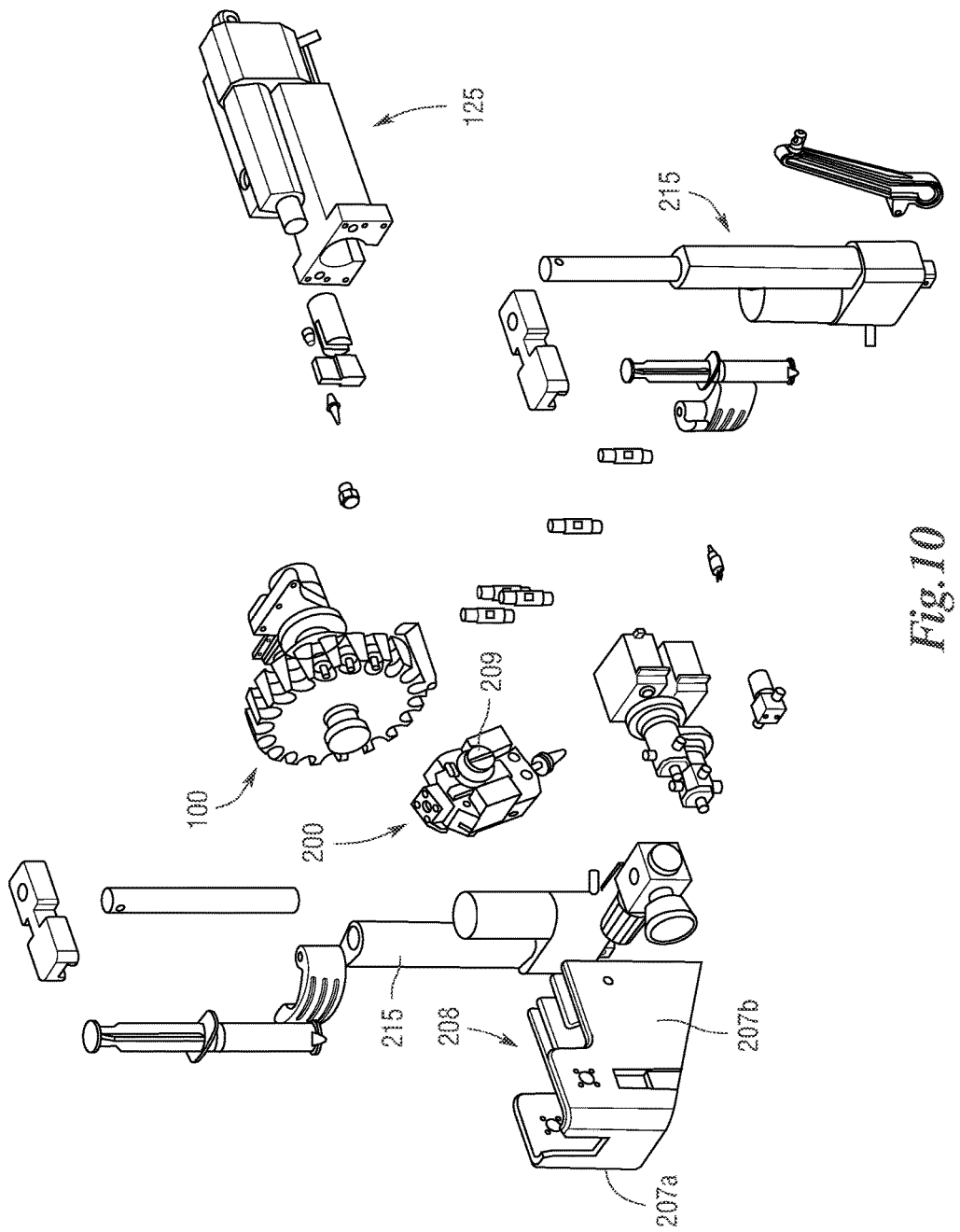
FIG. 10 depicts an exploded view of a driver for the reel assembly.
Figure 12:
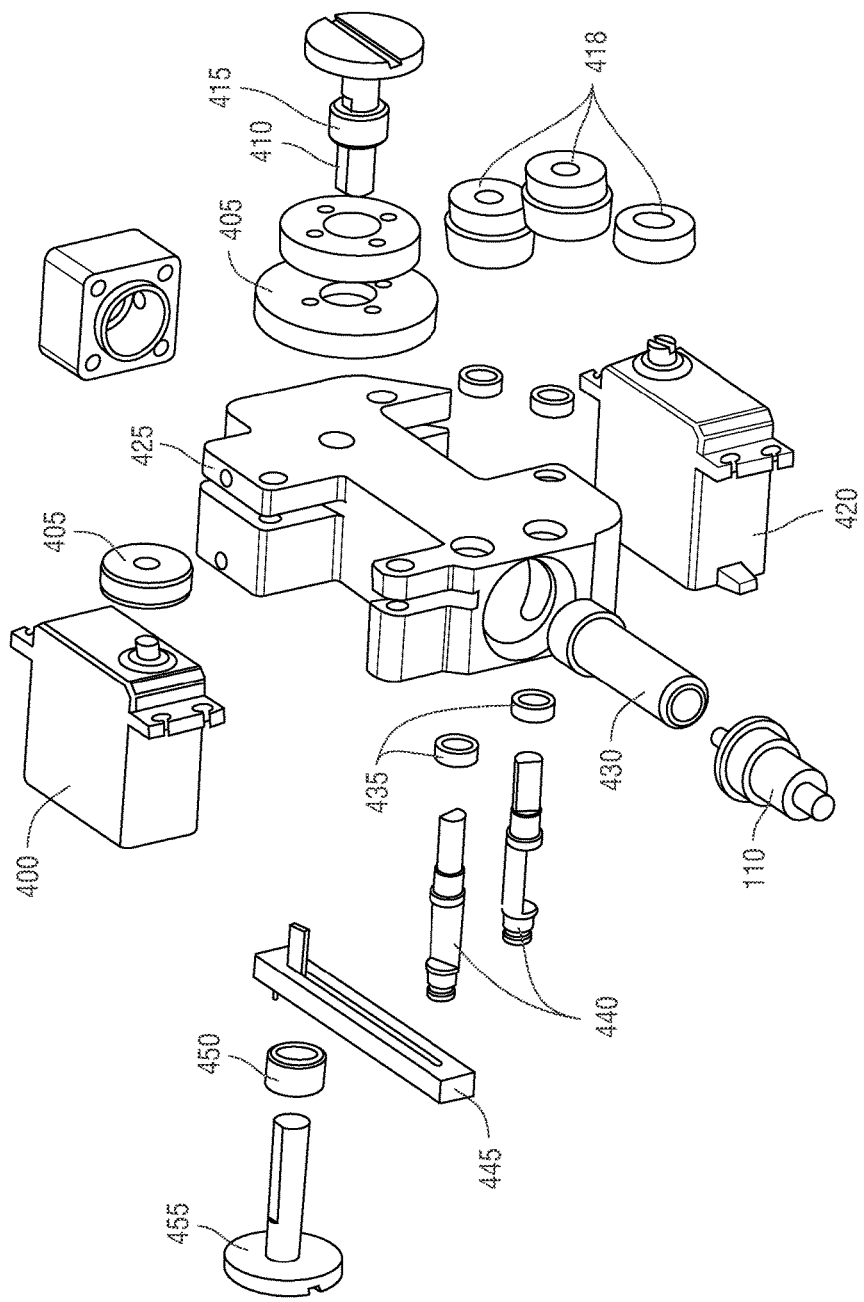
FIG. 12 depicts an exploded view of the gun assembly.

FIG. 10. depicts the gun assembly 200 and the linear electric actuator 215, which is driven by a gun servo 50 (further described in FIG. 12). The reel assembly 100 is also shown in communication with the linear actuator 125.

In another embodiment, the gun assembly 200 allows a cartridge 110 to receive ammonia nitrogen 13. A cartridge 110 is inserted into the gun housing interior 208 by way of the linear actuator 125. A spring loaded fitting connector (not shown) assures a good seal for the transfer of radioactive fluid, preferably ammonia nitrogen 13, through the cartridge 110. The radioactive fluid is then sent through ammonia nitrogen 13 output line 90 and supplied to vial 95.

After the cartridge 110 transfers the radioactive fluid, namely, the ammonia nitrogen 13, cartridge 110 is rinsed with water and saline, the linear actuator 125 retracts and the gun assembly 200 rotates (by way of linear electric actuator 215) down to eject the used cartridge 110 to the waste carafe 230. The gun assembly 200 rotates back to horizontal position for the next run.

Figure 11:
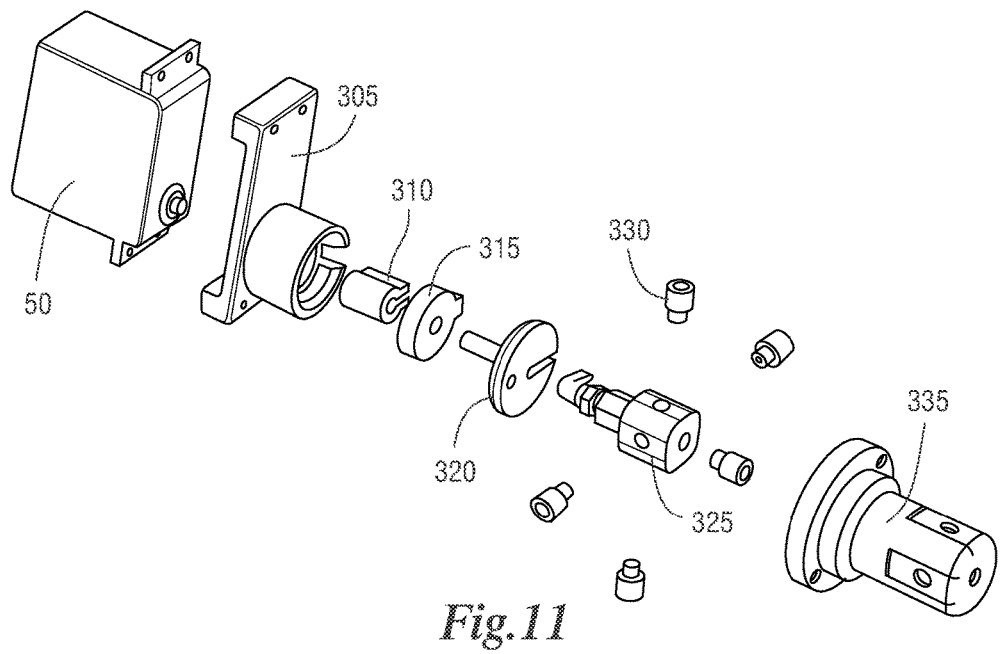
FIG. 11 depicts an exploded view of a gun servo drive.

FIG. 11 depicts the servo drive 50 connected to a servo frame 305, a servo shaft coupling 310, an angular position sensor 315, a shaft valve coupling 320, a valve 325, a PEEK fitting 330, and a servo cover 335.

FIG. 12 depicts a servo drive 400 which controls the position of the gun assembly 200. The servo 400 has gear drives 405, a shaft 410, a bearing 415, and additional gear drives 418. The servo 420 drives a cam cartridge locker 440 of a gun frame 425. The gun frame 425 has a cartridge front connector 430, a cam bearing 435, the cam cartridge locker 440, a linear cartridge sensor 445, a shaft bearing 450, and a gun frame shaft 455.

In another embodiment, a batch selector (not shown) is disclosed having a line input (not shown) from a system output line (not shown). The batch selector allows the delivery system 10 to select 1 of 20 batch production vials using a single production line input (not shown). In a preferred embodiment, the vials are 30 cc sterile vials. One benefit of this design is that it eliminates valves that are used to select the location of the receiving media to multiple location vials.

In another embodiment, a method of supplying with ammonia nitrogen 13 is disclosed. The method includes the steps of: supplying at least one anion cartridge 110 in a cartridge receiving recess 108 of the cartridge reel; installing a saline bag on a hook located on the left of the second side of the central support member 20; installing a sterile water bag 80 on a hook located on the right of the second side of the central support member 20; supplying sterile water to water bag 80, wherein the water bag 80 has a sensor and valve; installing a gas helium tank filled with helium within the second side of the central support member 20, wherein the gas helium tank has a pressure gauge and helium regulator 75 and is in communication with a valve; supplying saline to a saline bag, wherein the saline bag has a sensor and valve, installing two syringes within the second side of the central support member 20; turning on a gas helium tank; pressing a button on the second side of the central support member 20 to start the process, which will cause the gun assembly 200 to select an anion cartridge 110; rotating a first sterile vial to be in communication with a third inlet line connected to the gas helium tank; rotating a second sterile vial to be in communication with a plug port that is in communication with the anion cartridge 110, wherein the anion cartridge 110 retains the ammonia nitrogen 13, while allowing the impurities to pass through; performing a PSI check on the helium gas tank and sealing the lines up to the plug port at 50 PSI, thereby ensuring that the anion cartridge 110 is locked into the gun assembly 200; ensuring that the fittings are not leaking by introducing helium into the first sterile vial, the second sterile vial and the associated input lines; and checking that the pressure is maintained.

The method further includes the steps of: rotating the first sterile valve to be in communication with a first input line (not shown) to receive a target, in particular, ammonia nitrogen 13 (ammonia dump); rotating the second sterile vial to be in communication with a first outlet line that leads to a waste carafe; and stroking a saline syringe and stroking a sterile water syringe.

The method also further includes the steps of: supplying ammonia nitrogen 13 from an external cyclotron by introducing the ammonia nitrogen 13 into the first sterile vial via an input line 1; rotating first sterile vial to an output line in communication with the anion cartridge, thereby allowing the ammonia nitrogen 13 to enter the anion cartridge 110, which traps the ammonia nitrogen 13; rotating first sterile vial to be in communication with input line 2; introducing sterile water into the first sterile vial so as to rinse the first sterile vial; rotating first sterile vial to the output line in communication with the anion cartridge, thereby allowing the sterile water to enter the anion cartridge 110 and purify the ammonia nitrogen 13. The impurities from the ammonia nitrogen 13 are water soluble and thus will be washed out of the anion cartridge by the sterile water by way of an output line to a waste carafe, while the purified ammonia nitrogen 13 will remain in the anion cartridge.

The method also further includes the steps of: rotating first sterile vial to be in communication with a third input line and bleed the line with pressure; rotating the second sterile vial to a first, second, or third output line; rotating the first sterile vial to a fourth input line via an input line 2; introducing helium into a sterile vial via input line 3; introducing saline into the sterile vial via input line 4; supplying saline to the first sterile vial; rotating first sterile vial to the output line in communication with the anion cartridge 110, thereby allowing saline to enter the anion cartridge 110. The saline releases the ammonia nitrogen 13 from the anion cartridge 110. The ammonia nitrogen 13 is forced into a plug in communication with second sterile vial by way of an input line into the second sterile vial. The valve on the plug is opened so as to allow the ammonia nitrogen 13 into the input line, supplying the ammonia nitrogen 13 to the second sterile vial, which is rotated to a first, second, or third output line.

In the case where the second sterile vial is rotated to the first output line, the ammonia nitrogen 13 will go directly to a single vial. In the case where the second sterile vial is rotated to the second output line, the ammonia nitrogen 13 will go directly to a manual batch transfer selector. In the case where the second sterile vial is rotated to the third output line, the ammonia nitrogen 13 will go directly to an automatic batch transfer selector.

In a preferred embodiment, the number of anion cartridges supplied is 20. In a preferred embodiment, the ammonia target is supplied in an amount large enough to supply twenty runs, preferably, 20 ml. In another preferred embodiment, water is supplied in an amount of 500 ml to 1,000 ml. In a preferred embodiment, the helium is at a pressure of 50 psi. In a preferred embodiment, saline is supplied in an amount of 250-500 ml. In another preferred embodiment the saline syringe is filled to 15 ml and the sterile water syringe is filled to 30 ml.

In another embodiment, an automated bubble point filter test is performed on the ammonia nitrogen 13 before the fluid is supplied to the vial. The delivery system 10 ensures that the membrane (not shown) of the filter (not shown) is in good condition. The bubble point filter test includes the steps of: applying 50 PSI of pressure for 30 seconds; stopping the gas supply; and analyzing the pressure drop by a calibrated time.

If the pressure drop is below a predetermined threshold point, then the filter fails and the ammonia nitrogen 13 is not used. A new filter assembly (not shown) is required for each run.

It will be appreciated by those skilled in the art that while the System for Delivery of a Fluid Such As Ammonia Nitrogen 13 has been described in detail herein, the invention is not necessarily so limited and other examples, embodiments, uses, modifications, and departures from the embodiments, examples, uses, and modifications may be made without departing from the system and all such embodiments are intended to be within the scope and spirit of the appended claims.

What is claimed is:

1. A system for delivering fluid comprising:
a central support member having opposed first and second sides;
a front box extending from the first side of the central support member;
a linear actuator supported by the central support member and the linear actuator extends through the central support member;
a reel assembly having a shaft and a shaft bearing and the shaft bearing is supported by the central support member, and wherein the reel assembly has a cartridge reel that is mounted on the shaft such that the cartridge reel is spaced from the second side of the central support member and the cartridge reel is capable of being rotated, and the cartridge reel defines cartridge receiving recesses for supporting cartridges,
an another linear actuator supported by the central support member and the another linear actuator extends from the second side of the central support member and the another linear actuator is axially alignable with a cartridge supported in the cartridge receiving recess and the another linear actuator is capable of actuating and pushing the cartridge out of the cartridge receiving recess and wherein the another linear actuator is in communication with a first input line that is in fluid communication with a source of an input product and the first input line is in fluid communication with the cartridge such that the cartridge can be filled with the input product;
a gun assembly having a gun housing interior mounted to the central support member and the another linear actuator for pushing the cartridge filled with the input product into the gun assembly upon actuation of the another linear actuator, and wherein the gun is capable of piercing the cartridge; and
the gun assembly capable of receiving the cartridge and for causing the cartridge to be pierced such that the input product can be delivered to a vial and the vial filled with input product can be used for immediate testing purposes.

2. The system for delivering fluid according to claim 1 further wherein the input product is ammonia nitrogen 13.

3. The system for delivering fluid according to claim 2 further wherein the first input line is in fluid communication with a source of ammonia nitrogen 13 and the first input line is in fluid communication with the cartridge such that the cartridge can be filled with the ammonia nitrogen 13.

4. The system for delivering fluid according to claim 3 further including a second input line that is in fluid communication with the cartridge when the cartridge is disposed in the gun to fill the cartridge with a fluid and at the same time force the ammonia nitrogen 13 to flow in to a vial such that once filled with the ammonia nitrogen 13 the vial can be used for immediate testing purposes and at the same time the cartridge becomes a waste cartridge.

5. The system for delivering fluid according to claim 4 further wherein the cartridge reel defines at least twenty cartridge receiving recesses such that a plurality of vials filled with ammonia nitrogen 13 are capable of being produced.

6. The system for delivering fluid according to claim 4 further wherein the gun assembly is enclosed by a gun assembly housing that defines a gun housing interior that is mounted to the second side of the central support member, and wherein the gun assembly further includes two spaced apart gun mounts that are supported by the second side of the central support member and the two spaced apart gun mounts support a pivot rod and the two spaced apart gun mounts are disposed in the gun housing interior.

7. The system for delivering fluid according to claim 6 further wherein the gun assembly is pivotally mounted to pivot rod and a gun servo mechanism under the control of a computerized control system is supported by the spaced apart gun mounts and connected to the gun assembly and the gun servo mechanism is capable of tilting the gun assembly on the pivot rod such that the waste cartridge falls out of the gun assembly.

8. The system for delivering fluid according to claim 7 further including a waste carafe that defines a waste carafe interior and the waste carafe is supported on the first side of the central support member and the waste carafe is in fluid communication with a waste cartridge passageway.

9. The system for delivering fluid according to claim 8 further wherein the waste cartridge passageway is defined from the gun housing interior and wherein waste cartridges that fall out of the gun slide through the waste cartridge passageway and into the waste carafe.

10. The system according to claim 1 further including a servo driver connected to the shaft of the reel assembly for rotating the cartridge reel such that the cartridge reel can be rotated and aligned with the another linear actuator.

11. The system for delivering fluid according to claim 1 further including a driver for driving the linear actuator, and the servo driver for rotating the reel assembly and the driver for the linear actuator under the control of a computerized control system that is mounted to the first side of the central support member.

* * * * *